(12) United States Patent
Nayar

(10) Patent No.: US 9,468,618 B2
(45) Date of Patent: *Oct. 18, 2016

(54) TOPICAL PHARMACEUTICAL GEL COMPOSITION OF DICLOFENAC SODIUM

(71) Applicant: Gavis Pharmaceuticals, Somerset, NJ (US)

(72) Inventor: Bala Chandran Nayar, Somerset, NJ (US)

(73) Assignee: LUPIN ATLANTIS HOLDINGS SA (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/569,689

(22) Filed: Dec. 13, 2014

(65) Prior Publication Data

US 2016/0166524 A1    Jun. 16, 2016

Related U.S. Application Data

(63) Continuation-in-part of application No. 14/568,364, filed on Dec. 12, 2014.

(51) Int. Cl.
| | |
|---|---|
| *A61K 31/196* | (2006.01) |
| *A61K 9/06* | (2006.01) |
| *A61P 29/00* | (2006.01) |
| *A61K 9/00* | (2006.01) |
| *A61K 47/32* | (2006.01) |
| *A61K 47/18* | (2006.01) |
| *A61K 47/14* | (2006.01) |
| *A61K 47/10* | (2006.01) |
| *A61K 47/02* | (2006.01) |

(52) U.S. Cl.
CPC ............ *A61K 31/196* (2013.01); *A61K 9/0014* (2013.01); *A61K 9/06* (2013.01); *A61K 47/02* (2013.01); *A61K 47/10* (2013.01); *A61K 47/14* (2013.01); *A61K 47/183* (2013.01); *A61K 47/32* (2013.01)

(58) Field of Classification Search
None
See application file for complete search history.

(56) References Cited

U.S. PATENT DOCUMENTS

2007/0269393 A1* 11/2007 Wepfer ............... A61K 9/06
424/59
2012/0220962 A1* 8/2012 Hsu ............... A61K 9/0014
604/307

FOREIGN PATENT DOCUMENTS

GR    WO 2006134406 A1 * 12/2006 ........... A61K 9/0014

* cited by examiner

*Primary Examiner* — H. Sarah Park
(74) *Attorney, Agent, or Firm* — McNeely, Hare & War, LLP; William D. Hare

(57) ABSTRACT

A topical pharmaceutical gel composition of diclofenac sodium suitable for once-a-day topical application is provided. The topical gel composition contains at least about 10 % w/w of diclofenac sodium and once-a-day application of the composition provides relief from pain or inflammation comparable to that achieved with four times daily application of diclofenac sodium 1 % or 3 % topical gel.

20 Claims, No Drawings

TOPICAL PHARMACEUTICAL GEL COMPOSITION OF DICLOFENAC SODIUM

CROSS-REFERENCE TO RELATED APPLICATION

The present application is a continuation-in-part of and claims priority to U.S. patent application Ser. No. 14/568,364, titled Topical Pharmaceutical Gel Composition of Diclofenac Sodium, filed on Dec. 12, 2014, the contents of which are incorporated herein in their entirety by reference.

BACKGROUND OF THE INVENTION (a) Field of the Invention

The present invention is directed to novel topical pharmaceutical gel compositions of diclofenac sodium. The topical compositions comprise at least about 10% w/w of diclofenac sodium and are suitable for once-a-day application. The invention is further directed to the use of said compositions for treating painful conditions, inflammations and/or rheumatic diseases or providing relief of the pain of osteoarthritis of joints amenable to topical treatment, such as the knees, ankles, feet, elbows, wrists, hands, spine, hip, and shoulder. Additionally, the present invention provides a method of manufacture of said composition.

(b) Description of the Related Art

Delivery of active agents across the skin or mucosal membrane is convenient, pain-free, non-invasive and circumvents problems associated with the "first pass effect". Such transdermal or topical drug delivery is typically restricted to low molecular weight drugs and drugs with specific lipophilic/hydrophilic balance able to penetrate the stratum corneum.

Transdermal drug delivery systems enable chemical modification of the barrier properties of the skin to effectively and efficiently permit permeation thereof. Known drawbacks of transdermal delivery systems are, for example, the length of time needed for permeation, a frequent dosing regimen, and the volume size of a transdermal composition needed to transdermally deliver a sufficient therapeutic amount of the active agent.

Diclofenac (2-(2,6-dichloranilino) phenylacetic acid) is a non-steroidal anti-inflammatory drug (NSAID) used to reduce inflammation and, as an analgesic, to reduce pain. It is available in the sodium, potassium, epolamine and diethylamine salt forms in numerous dosage forms (oral tablet, oral syrup, topical gel, cataplasm, ophthalmic drop, suppository, etc.).

An example of a well-known transdermal diclofenac formulation is Voltaren® Gel 1 which comprises 1% diclofenac sodium. Voltaren® is indicated in the USA for the relief of the pain due to osteoarthritis of joints amenable to topical treatment, including the knees, ankles, feet, elbows, wrists, and hands. Up to 4 gm of Voltaren® gel can be applied to lower extremities (including the knees, the ankles, and the feet) 4 times daily so that up to not more than 16 gm daily of Voltaren® Gel 1% is applied to any single joint of the lower extremities. Up to 2 gm of Voltaren® Gel 1% can also be applied to the upper extremities (which include the elbows, the wrists and the hands) 4 times daily so that up to not more than 8 gm daily of Voltaren® Gel 1% is applied to any single joint of the upper extremities. Overall, the total dose of Voltaren® Gel 1% should not exceed 32 gm per day over all affected joints. Neither the total amount (up to 32 gm per day) nor the frequency of application (4 times a day) are satisfactory from a patient perspective.

U.S. Pat. No. 7,335,379 discloses formulations for transdermal or transmucosal administration of active agents, such as diclofenac, containing an alkanol, a polyalcohol, a monoalkyl ether of diethylene glycol and a fatty alcohol with a fatty alcohol content of up to 2%.

U.S. Pat. No. 4,543,251 discloses an external gel formulation containing 0.3 to 3% w/w of diclofenac sodium having good stability.

PCT Application Publication No. 2014009241 discloses diclofenac gel formulations containing 1% and 3% diclofenac sodium, $C_2$ to $C_4$ alkanol, monoalkyl ether of diethylene glycol and fatty alcohol.

U.S. Pat. No. 7,132,452 discloses topical formulations containing NSAID, particularly diclofenac for alleviating pain/inflammation associated with infection caused by herpes virus. The amount of diclofenac in the formulation can be 1-10% w/w of the entire formulation. The patent further discloses that the formulation provides a complete relief on application for seven days.

EP 1,890,687 B1 discloses topical gel formulations of diclofenac sodium for relief of pain and inflammation. According to the patent the formulation may contain up to 10% w/w of diclofenac.

None of the prior art reference disclose or suggest topical gel formulation containing high amount of diclofenac sodium, let alone its therapeutic benefits on once-a-day application.

There remains a need for topical compositions of diclofenac containing relatively higher amount of diclofenac sodium which are effective for treating painful conditions, inflammations, and specifically providing fast and effective treatment for alleviating symptoms relating to the pain of osteoarthritis of joints. On comparing to the topical treatment of Voltaren® Gel 1% or other commercially available 3% diclofenac gel formulations, the topical composition of the present invention on once-a-day application provided relief that is comparable to that achieved with 4 times daily application of currently known 1% w/w or 3% w/w diclofenac gel formulations.

SUMMARY OF THE INVENTION

The present invention provides a topical pharmaceutical gel composition configured for and suitable for once-a-day application of diclofenac sodium.

In one aspect, the invention provides a topically applied pharmaceutical gel composition suitable for once-a-day application of diclofenac sodium comprising diclofenac sodium in an amount of at least about 10% w/w of the composition. Once-a-day application of the pharmaceutical gel composition provides steady state blood levels of diclofenac that are comparable to steady state blood levels of diclofenac achieved with 4 times daily application of diclofenac sodium 1% or 3% topical gel.

In an embodiment of this aspect, the diclofenac sodium gel is used for the relief of joint pain of osteoarthritis in the knees, ankles, feet, elbows, wrists, and hands. In another embodiment, the diclofenac sodium gel is used for the relief of joint pain of osteoarthritis in the spine, hip, and shoulder.

In another aspect, once-a-day administration of said composition provides steady state blood levels of diclofenac in the range of about 5 ng/ml to about 30 ng/ml.

In another aspect, once-a-day administration of said composition provides steady state blood $C_{max}$ levels of diclofenac in the range of about 5 ng/ml to about 50 ng/ml.

In another aspect, once-a-day administration of said composition provides steady state blood $C_{min}$ levels of diclofenac in the range of about 5 ng/ml to about 20 ng/ml.

In another aspect, once-a-day administration of said composition provides steady state AUC in the range of about 10 ng/ml*hr to about 100 ng/ml*hr.

In another aspect, the topical pharmaceutical gel composition of diclofenac sodium comprises a glycol solvent, at least one gelling agent, at least one preservative, at least one antioxidant, salicylic acid ester, menthol, water, and at least one acidic and/or basic agent.

In another aspect, the topical pharmaceutical gel composition of diclofenac sodium consists essentially of diclofenac sodium, a glycol solvent, at least one gelling agent, at least one preservative, at least one antioxidant, salicylic acid ester, menthol, water, and at least one acidic and/or basic agent.

In another aspect, the topical pharmaceutical gel composition of diclofenac sodium consists of diclofenac sodium, a glycol solvent, at least one gelling agent, at least one preservative, at least one antioxidant, salicylic acid ester, menthol, water, and at least one acidic and/or basic agent.

In another aspect, the topical pharmaceutical gel composition of diclofenac sodium comprises:
- at least about 10% w/w of diclofenac sodium,
- about 5-25% w/w of a glycol solvent,
- about 1-6% w/w of at least one gelling agent,
- about 0.01-0.75% w/w of at least one preservative,
- about 0.01-1% w/w of at least one antioxidant,
- about 1-10% w/w of salicylic acid ester,
- about 0.05-1% w/w of menthol,
- at least 50% w/w of water, and
- at least one acidic and/or basic agent to adjust the pH of the composition to 4-8.

In one embodiment, the amount of diclofenac sodium in the gel composition of the invention is between about 10-14% w/w, such as about 10% w/w, about 12% w/w or about 14% w/w.

In another embodiment, the topical pharmaceutical gel composition is devoid of either $C_2$ to $C_4$ alkanol, monoalkyl ether of diethylene glycol, or a fatty alcohol. Also provided is a topically applicable diclofenac sodium gel composition which is stable at room temperature. Methods of treating painful conditions and inflammations or providing fast and effective treatment for alleviating symptoms relating to the pain of osteoarthritis of joints using these compositions are further provided by the invention.

In another aspect, the invention provides a topical pharmaceutical gel composition suitable for once-a-day application of diclofenac sodium comprising a glycol solvent selected from the group consisting of propylene glycol, polyethylene glycol, ethylene glycol, butylene glycol, and hexalylene glycol. In one embodiment, the glycol solvent in the gel composition is propylene glycol. In further embodiments, the amount of glycol solvent present in the gel composition is about 5-25% w/w.

In another aspect, the invention provides a topical pharmaceutical gel composition suitable for once-a-day application of diclofenac sodium. The topical gel composition comprises a gelling agent selected from the group consisting of hydroxypropyl cellulose and carbomers. In one embodiment, the gelling agent in the gel composition is carbomer. In further embodiments, the amount of gelling agent present in the gel composition is about 1-6% w/w.

In another aspect, the invention provides a topical pharmaceutical gel composition suitable for once-a-day application of diclofenac sodium comprising preservatives selected from the group consisting of methyl paraben, propyl paraben, chlorocresol, thomersal, sorbic acid, potassium sorbate and mixtures thereof. In one embodiment, the preservatives in the gel composition are methyl paraben and propyl paraben. In further embodiments, the amount of preservatives present in the gel composition is about 0.01-0.75% w/w.

In another aspect, the invention provides a topical pharmaceutical gel composition suitable for once-a-day application of diclofenac sodium comprising an antioxidant selected from the group consisting of edetate disodium, sodium metabisulfite, propyl gallate, and edetate trisodium. In one embodiment, the antioxidant in the gel composition is edetate disodium. In further embodiments, the amount of antioxidant present in the gel composition is about 0.01-1% w/w.

In another aspect, the invention provides a topical pharmaceutical gel composition suitable for once-a-day application of diclofenac sodium comprising a salicylate ester selected from the group consisting of methyl salicylate, ethyl salicylate and glycol monosalicylate. In one embodiment, the salicylate ester in the gel composition is methyl salicylate. In further embodiments, the amount of salicylate ester present in the gel composition is about 1-10% w/w.

In another aspect, the invention provides a topical pharmaceutical gel composition suitable for once-a-day application of diclofenac sodium comprising propylene glycol, carbomers, edetate disodium, methyl salicylate, menthol and sodium hydroxide.

In another aspect, the topical pharmaceutical gel of the invention is devoid of either $C_2$ to $C_2$ to $C_4$ alkanol, monoalkyl ether of diethylene glycol, or fatty alcohol.

In another aspect, the viscosity of the topical pharmaceutical gel of the invention is in the range of about 60,000 to 600,000 cps.

In another aspect, the invention provides a method for the manufacture of the topically applied diclofenac sodium gel composition, which process comprises the steps of:
(a) dissolving diclofenac sodium, gelling agent, antioxidant and preservative in water;
(b) dissolving preservative, salicylate ester and menthol in glycol solvent;
(c) adding the solvent mixtures of steps (a) and (b) together and mixing under high shear homogenization; and
(d) adjusting the pH of the mixture with basic and/or acid agent to a pH in the range of about 4 to 6.

In another aspect, the invention provides a method for the treatment of painful conditions, inflammations and/or rheumatic diseases comprising topically applying to a patient in need thereof the gel composition as described herein. The gel composition may be used for the relief of joint pain of osteoarthritis in the knees, ankles, feet, elbows, wrists, and hands. The gel composition may be used for the relief of joint pain of osteoarthritis in the spine, hip, and shoulder.

Still other aspects and advantages of the invention will be apparent from the following detailed description of the invention.

DETAILED DESCRIPTION OF THE INVENTION

The invention provides for a topical pharmaceutical gel composition suitable for once-a-day topical application of diclofenac sodium. Preferably, the composition contains or consists essentially of, at least, a combination of a salicylate ester and menthol along with other components.

The invention addresses the need for topical gel formulations of diclofenac sodium which require only once-a-day application and provide relief which is comparable to that achieved by 4 times daily application of commercially available diclofenac sodium 1% or 3% formulations, such as Voltaren® 1% Gel.

The invention, for example, provides topical gel formulation of diclofenac sodium containing about 10% w/w to about 15% w/w of diclofenac sodium. The inventors have observed that a particular formulation of diclofenac sodium requires only single application in a day as compared to the frequent application required for commercially available diclofenac gel formulations.

In one embodiment, once-a-day application of said pharmaceutical gel composition provides steady state blood levels of diclofenac that are comparable to steady state blood levels of diclofenac achieved with 4 times daily application of diclofenac sodium 1% or 3% topical gel.

In one aspect, use of the term "comparable" with respect to achieving steady state blood levels of diclofenac comparable to a 1% or 3% topical gel means that the once daily application of the composition of the invention is bioequivalent to the commercially available 1% or 3% topical gel topically applied four times daily. As well understood by one of skill in the art, bioequivalence has the term used by the US Food and Drug Administration when comparing a test product to a reference product.

In this aspect, the compositions are expected to be bioequivalent to a topically administered diclofenac sodium topical gel product with 1% to 3% w/w diclofenac sodium that is topically administered four times per day. The in vivo bioavailability determinations for demonstrating bioequivalence can use plasma concentrations to assess maximum plasma concentration ($C_{max}$) and area under the curve (AUC). Bioequivalence is established by comparing pharmacokinetic parameters, for example AUC and $C_{max}$, of the present invention with the Voltaren® 1% topical gel in healthy human subjects. The term "AUC" refers to the area under the time/plasma concentration curve after the administration of the diclofenac sodium topical dosage form to healthy human subjects. The term "$C_{max}$" refers to the maximum concentration of diclofenac sodium in the blood following the administration of the diclofenac sodium topical dosage form to healthy human subjects. Generally, to show bioequivalence, the 90% confidence interval of the AUC and $C_{max}$ values of the test product should be within a range of 80% to 125% of the reference product (e.g., Voltaren® Gel 1%). The values of the excipients can be varied as known by one of skill in the art to achieve bioequivalence.

Once-a-day administration of said composition provides steady state blood levels of diclofenac in the range of about 5 ng/ml to about 30 ng/ml, steady state blood $C_{max}$ levels of diclofenac in the range of about 5 ng/ml to about 50 ng/ml, steady state blood $C_{min}$ levels of diclofenac in the range of about 5 ng/ml to about 20 ng/ml, and steady state AUC in the range of about 10 ng/ml*hr to about 100 ng/ml*hr.

The inventors have further observed that topical gel formulations of diclofenac sodium in accordance with the invention is storage stable at a temperature of about 40° C. and relative humidity of about 75% for a period of at least 3 months.

In one embodiment, the topical pharmaceutical gel composition suitable for once-a-day application of diclofenac sodium comprises:
at least about 10% w/w of diclofenac sodium,
about 5-25% w/w of a glycol solvent,
about 1-6% w/w of at least one gelling agent,
about 0.01-0.75% w/w of at least one preservative,
about 0.01-1% w/w of at least one antioxidant,
about 1-10% w/w of salicylic acid ester,
about 0.05-1% w/w of menthol,
at least 50% w/w of water, and
at least one acidic and/or basic agent to adjust the pH of the composition to 4-8.

In another embodiment, the amount of diclofenac sodium in the gel composition of the invention is about 10% w/w, about 12% w/w or about 14% w/w.

In a further embodiment, the topical pharmaceutical gel composition is devoid of either $C_2$ to $C_4$ alkanol, monoalkyl ether of diethylene glycol or fatty alcohol.

In an embodiment, viscosity of the topical pharmaceutical gel composition is in the range of about 60,000 to 600,000 cps.

In another aspect, the invention provides a topically applied pharmaceutical gel composition intended for and suitable for once-a-day application of diclofenac sodium. The topical pharmaceutical gel composition intended for and suitable for once-a-day topical administration consists of or consists essentially of: (a) about 10-15% w/w of diclofenac sodium; (b) about 5-25% w/w of a glycol solvent; (c) about 1-6% w/w of at least one gelling agent; (d) about 0.01-0.75% w/w of at least one preservative; (e) about 0.01-1% w/w of at least one antioxidant; (f) about 1-10% w/w of salicylic acid ester; (g) about 0.05-1% w/w of menthol; (h) at least 50% w/w of water; and (i) at least one acidic and/or basic agent to adjust the pH of the composition to 4-8.

Embodiments of this aspect may consist of or consist essentially of about (a) 10-15% w/w of diclofenac sodium; (b) about 5-25% w/w of propylene glycol as the glycol solvent; (c) about 1-6% w/w of carbomer as the gelling agent; (d) about 0.01-0.75% w/w of methyl paraben and propyl paraben as the preservative; (e) about 0.01-1% w/w of at least one edetate disodium as the antioxidant; (f) about 1-10% w/w of methyl salicylate as the salicylic acid ester; (g) about 0.05-1% w/w of menthol; (h) at least 50% w/w of water; and (i) at least one acidic and/or basic agent to adjust the pH of the composition to 4-8.

Another embodiment of this aspect may consist of or consist essentially of (a) about 10% w/w of diclofenac sodium; (b) about 10% w/w of propylene glycol as the glycol solvent; (c) about 3.5% w/w of carbomer as the gelling agent; (d) about 0.4% w/w of methyl paraben and propyl paraben as the preservative; (e) about 0.17% w/w of at least one edetate disodium as the antioxidant; (f) about 3% w/w of methyl salicylate as the salicylate acid ester; (g) about 0.2% w/w of menthol; (h) at least 50% w/w of water; and (i) at least one acidic and/or basic agent to adjust the pH of the composition to 4-8.

Another embodiment of this aspect may consist of or consist essentially of (a) about 14% w/w of diclofenac sodium; (b) about 20% w/w of propylene glycol as the glycol solvent; (c) about 2.5% w/w of carbomer as the gelling agent; (d) about 0.4% w/w of methyl paraben and propyl paraben as the preservative; (e) about 0.17% w/w of at least one edetate disodium as the antioxidant; (f) about 7% w/w of methyl salicylate as the salicylate acid ester; (g) about 0.3% w/w of menthol; (h) at least 50% w/w of water; and (i) at least one acidic and/or basic agent to adjust the pH of the composition to 4-8.

In these embodiments consisting of or consisting essentially of particular excipients to provide a composition suitable for once daily topical administration, the topical pharmaceutical gel composition is devoid of either $C_2$ to $C_4$ alkanol, monoalkyl ether of diethylene glycol, or fatty alcohol.

Suitable glycols include, by way of example and without limitation, propylene glycol, polyethylene glycol, ethylene glycol, butylene glycol, and hexalylene glycol. A preferred glycol is polyethylene glycol. The glycol is preferably present in an amount of about 5-25% w/w.

Suitable gelling agent include, by way of example and without limitation, carbomers, xanthan gum, acacia, tragacanth, sodium alginate, gelatin, modified starches, hydroxypropyl cellulose, hydroxyethyl cellulose, hydroxypropyl methylcellulose, hydroxypropyl methylcellulose phthalate, methyl cellulose, co-polymers formed between maleic anhydride and methyl vinyl ether, methacrylate derivatives, polyethylene oxides, polyoxyethylene-polyoxypropylene copolymers, polyvinyl alcohol and mixtures thereof. A preferred gelling agent is carbomer. The gelling agent is preferably present in an amount of about 1-6% w/w.

Carbomers, in the context of the present invention, are defined as homo- or copolymers of acrylic acid that are cross-linked, e.g. with an allyl ether of pentaerythritol (allyl pentaerythritol) or an allyl ether of sucrose (allyl sucrose). Copolymers are formed e.g. with minor levels of long chain alkyl acrylate co-monomers. Homopolymers are preferred. Non limiting examples of carbomers are carbomer 940, 971, 973, 974, 980, 981, 941, 974, 934 and 910. Especially preferred are carbomers 980, 940, 981, 941, 974, 934 and 910. Preferably, carbomers are present in an amount of from about 1-6% w/w.

Suitable preservatives include, by way of example and without limitation methyl paraben, propyl paraben, chlorocresol, thomersal, sorbic acid, potassium sorbate and mixtures thereof. Preferred preservatives are a combination of methyl paraben and propyl paraben. The preservatives are preferably present in an amount of about 0.01-0.75% w/w.

A suitable salicylic acid ester includes, by way of example and without limitation, methyl salicylate, ethyl salicylate and glycol monosalicylate. A preferred salicylic acid ester is methyl salicylate. The salicylic acid ester is preferably present in an amount of about 0.01-0.75% w/w. In another embodiment, the ratio of amount of diclofenac sodium to salicylic acid ester is preferably in the range of about 1:0.1 to about 1:0.5.

Suitable antioxidant include, by way of example and without limitation, edetate disodium, sodium sulphite, sodium metabisulfite, propyl gallate, edetate trisodium, tocopherol derivatives, butylated hydroxyl toluene, butylated hydroxyl anisole, ascorbic acid, fumaric acid, malic acid, and citric acid. A preferred antioxidant is edetate disodium. The antioxidant is preferably present in an amount of about w/w. 0.01-1% w/w.

Suitable basic agents include, by way of example and without limitation, sodium hydroxide, potassium hydroxide and ammonia. A preferred basic agent is sodium hydroxide.

Suitable acidic agents include, by way of example and without limitation, hydrochloric acid, acetic acid, lactic acid and citric acid. A preferred acidic agent is hydrochloric acid.

In one embodiment, the ratio of amount of diclofenac sodium to menthol is preferably in the range of about 1:0.01 to about 1:0.05.

The topical gel composition of the present invention may further comprise at least one additional ingredient selected from buffering agents, moisturizing agents, humectants, surfactants, neutralizing agents, chelating agents, and emollients.

In another embodiment, the topical pharmaceutical gel composition suitable for once-a-day application of diclofenac sodium comprises:
  about 10% w/w of diclofenac sodium,
  about 10% w/w of propylene glycol,
  about 3.5% w/w of carbomer,
  about 0.4% w/w of methyl paraben and propyl paraben,
  about 0.17% w/w of at least one edetate disodium,
  about 3% w/w of methyl salicylate,
  about 0.2% w/w of menthol,
  at least 50% w/w of water, and
  at least one acidic and/or basic agent to adjust the pH of the composition to 4-8.

In another embodiment, the topical pharmaceutical gel composition suitable for once-a-day application of diclofenac sodium comprises:
  about 14% w/w of diclofenac sodium,
  about 20% w/w of propylene glycol,
  about 2.5% w/w of carbomer,
  about 0.4% w/w of methyl paraben and propyl paraben,
  about 0.17% w/w of at least one edetate disodium,
  about 7% w/w of methyl salicylate,
  about 0.3% w/w of menthol
  at least 50% w/w of water; and
  at least one acidic and/or basic agent to adjust the pH of the composition to 4-8.

The invention further provides a method for the manufacture of a topical gel formulation of diclofenac sodium. The method includes the following steps:
  (a) dissolving diclofenac sodium, gelling agent, antioxidant and preservative in water;
  (b) dissolving preservative, salicylate ester and menthol in glycol solvent;
  (c) adding solvent mixture of step (a) and (b) together and mixing under high shear homogenization; and
  (d) adjusting the pH of mixture with basic and/or acid agent to a pH in the range of about 4 to 6.

In another embodiment, the method for the manufacture of topical gel formulation of diclofenac sodium includes the following steps:
  (a) dissolving diclofenac sodium, carbomer, edetate sodium and methylparaben in water;
  (b) dissolving propylparaben, methylsalicylate and menthol in propylene glycol;
  (c) adding solvent mixture of step (a) and (b) together and mixing under high shear homogenization; and
  (d) adjusting the pH with sodium hydroxide and/or hydrochloric acid to a pH in the range of about 4 to 6.

The topical gel formulation of diclofenac sodium of the invention may be topically applied to the affected areas of the skin to a patient suffering from painful conditions, inflammations and/or rheumatic diseases or for providing relief of the pain of osteoarthritis of joints.

EXAMPLE 1

Diclofenac Sodium 10% w/w Topical Gel

TABLE 1

| Sr. No. | Ingredients | Quantity % w/w |
|---|---|---|
| 1 | Diclofenac Sodium | 10.00 |
| 2 | Carbomer | 3.50 |
| 3 | Edetate Disodium | 0.17 |

TABLE 1-continued

| Sr. No. | Ingredients | Quantity % w/w |
|---|---|---|
| 4 | Methylparaben | 0.30 |
| 5 | Propylparaben | 0.08 |
| 6 | Propylene Glycol | 10.00 |
| 7 | Methyl Salicylate | 3.00 |
| 8 | Menthol | 0.10 |
| 9 | Purified Water | QS |
| 10 | Sodium Hydroxide (to adjust pH to ~4-6) | QS |

Process: Diclofenac sodium, carbomer, edetate sodium and methyl paraben were dissolved in water. Separately, propyl paraben, methyl salicylate and menthol were dissolved in propylene glycol. The two solutions were added together, mixed under high shear homogenization and the pH of the mixture was adjusted to 4 to 6 with sodium hydroxide and/or hydrochloric acid. The viscosity of the gel measured was in the range of about 60,000 to 600,000 cps.

EXAMPLE 2

Diclofenac Sodium 12% w/w Topical Gel

TABLE 2

| Sr. No. | Ingredients | Quantity % w/w |
|---|---|---|
| 1 | Diclofenac Sodium | 12.00 |
| 2 | Carbomer | 3.00 |
| 3 | Edetate Disodium | 0.17 |
| 4 | Methylparaben | 0.30 |
| 5 | Propylparaben | 0.08 |
| 6 | Propylene Glycol | 15.00 |
| 7 | Methyl Salicylate | 5.00 |
| 8 | Menthol | 0.20 |
| 9 | Purified Water | QS |
| 10 | Sodium Hydroxide (to adjust pH to ~4-6) | QS |

Process: The gel formulation was prepared by the process as per Example 1. The pH of the mixture was adjusted to 4 to 6 with sodium hydroxide and/or hydrochloric acid and viscosity of the gel was measured in the range and found to be in the range of about 60,000 to 600,000 cps.

EXAMPLE 3

Diclofenac Sodium 14% w/w Topical Gel

TABLE 3

| Sr. No. | Ingredients | Quantity % w/w |
|---|---|---|
| 1 | Diclofenac Sodium | 14.00 |
| 2 | Carbomer | 2.50 |
| 3 | Edetate Disodium | 0.17 |
| 4 | Methylparaben | 0.30 |
| 5 | Propylparaben | 0.08 |
| 6 | Propylene Glycol | 20.00 |
| 7 | Methyl Salicylate | 7.00 |
| 8 | Menthol | 0.3 |
| 9 | Purified Water | QS |
| 10 | Sodium Hydroxide (to adjust pH to ~4-6) | QS |

Process: Diclofenac sodium, carbomer, edetate sodium and methyl paraben were dissolved in water. Separately, propyl paraben, methyl salicylate and menthol were dissolved in ethyl alcohol. The remainder of the formulation was prepared by the process as per Example 1. The pH of the mixture was adjusted to 4 to 6 with sodium hydroxide and/or hydrochloric acid and the viscosity of the gel measured was in the range of about 60,000 to 600,000 cps.

What is claimed is:

1. A topically applied pharmaceutical gel composition suitable for once-a-day topical application of diclofenac sodium comprising diclofenac sodium, salicylic acid ester, and menthol, for the relief of joint pain of osteoarthritis in one or more of the knees, ankles, feet, elbows, wrists, hands, spine, hip, or shoulder, the diclofenac sodium being present in the composition in an amount of at least about 10% w/w of the composition, wherein once-a-day topical application of said pharmaceutical gel composition provides steady state blood levels of diclofenac that are comparable to steady state blood levels of diclofenac achieved with four times daily topical application of diclofenac sodium 1% or 3% w/w topical gel, wherein the ratio of the amount of diclofenac sodium to the amount of salicylic acid ester is about 1:0.1 to about 1:0.5 and/or the ratio of the amount of diclofenac sodium to the amount of menthol is about 1:0.01 to about 1:0.05.

2. A gel composition comprising:
diclofenac sodium, a glycol solvent, at least one gelling agent, at least one preservative, at least one antioxidant, salicylic acid ester, menthol, water; and at least one acidic and/or basic agent and is devoid of a $C_2$ to $C_4$ alkanol, monoalkyl ether of diethylene glycol, or fatty alcohol;
wherein the ratio of the amount of diclofenac sodium to the amount of salicylic acid ester is about 1:0.1 to about 1:0.5 and the ratio of the amount of diclofenac sodium to the amount of menthol is about 1:0.01 to about 1:0.05.

3. The gel composition of claim 2, wherein once-a-day administration of said composition provides steady state blood levels of diclofenac in the range of about 5 ng/ml to about 30 ng/ml.

4. The gel composition of claim 2, wherein once-a-day administration of said composition provides steady state blood $C_{max}$ levels of diclofenac in the range of about 5 ng/ml to about 50 ng/ml, steady state blood $C_{min}$ levels of diclofenac in the range of about 5 ng/ml to about 20 ng/ml, and steady state AUC in the range of about 10 ng/ml*hr to about 100 ng/ml*hr.

5. The gel composition of claim 2, wherein the composition comprises a glycol solvent, at least one gelling agent, at least one preservative, at least one antioxidant, salicylic acid ester, menthol, water; and at least one acidic and/or basic agent and is devoid of a $C_2$ to $C_4$ alkanol, monoalkyl ether of diethylene glycol, or fatty alcohol.

6. The gel composition of claim 5, wherein the glycol solvent is selected from the group consisting of propylene glycol, polyethylene glycol, ethylene glycol, butylene glycol, and hexylene glycol.

7. The gel composition of claim 5, wherein the gelling agent is selected from the group consisting of carbomers, xanthan gum, acacia, tragacanth, sodium alginate, gelatin, modified starches, hydroxypropyl cellulose, hydroxyethyl cellulose, hydroxypropyl methylcellulose, hydroxypropyl methylcellulose phthalate, methyl cellulose, co-polymers formed between maleic anhydride and methyl vinyl ether, methacrylate derivatives, polyethylene oxides, polyoxyethylene-polyoxypropylene copolymers, polyvinyl alcohol and mixtures thereof.

8. The gel composition of claim 5, wherein the preservatives are selected from the group consisting of methyl paraben, propyl paraben, chlorocresol, thiomersal, sorbic acid, potassium sorbate, individually and as mixtures thereof.

9. The gel composition of claim 5, wherein the antioxidant is selected from the group consisting of edetate disodium, sodium sulphite, sodium metabisulfite, propyl gallate, edetate trisodium, tocopherol derivatives, butylated hydroxyl toluene, butylated hydroxyl anisole, ascorbic acid, fumaric acid, malic acid, and citric acid.

10. The gel composition of claim 5, wherein the salicylic acid ester is selected from the group consisting of methyl salicylate, ethyl salicylate and glycol monosalicylate.

11. The gel composition of claim 5, wherein the acidic and basic agents are selected from the group consisting of sodium hydroxide, potassium hydroxide, ammonia, hydrochloric acid, acetic acid, lactic acid and citric acid.

12. A method for the treatment of painful conditions, inflammations and/or rheumatic diseases comprising topically applying the gel composition of claim 2 to a patient in need thereof.

13. A method of treating or providing the relief of joint pain of osteoarthritis in one or more of the knees, ankles, feet, elbows, wrists, hands, spine, hip, and shoulder, the method comprising topically applying once per day a pharmaceutical gel composition comprising diclofenac sodium, a glycol solvent, at least one gelling agent, at least one preservative, at least one antioxidant, salicylic acid ester, menthol, water; and at least one acidic and/or basic agent and is devoid of a $C_2$ to $C_4$ alkanol, monoalkyl ether of diethylene glycol, or fatty alcohol; wherein the ratio of the amount of diclofenac sodium to the amount of salicylic acid ester is about 1:0.1 to about 1:0.5 and/or the ratio of the amount of diclofenac sodium to the amount of menthol is about 1:0.01 to about 1:0.05, wherein the diclofenac sodium is in the topical composition in an amount of at least about 10% w/w of the composition, wherein once-a-day topical application of the pharmaceutical gel composition provides steady state blood levels of diclofenac that are comparable to steady state blood levels of diclofenac achieved with four times daily topical application of diclofenac sodium 1% or 3% w/w topical gel.

14. The method of claim 13, wherein topically applying a pharmaceutical gel composition of diclofenac sodium comprises applying a pharmaceutical gel composition further comprising:
about 5-25% w/w of a glycol solvent;
about 1-6% w/w of at least one gelling agent;
about 0.01-0.75% w/w of at least one preservative;
about 0.01-1% w/w of at least one antioxidant;
about 1-10% w/w of salicylic acid ester;
about 0.05-1% w/w of menthol;
at least 50% w/w of water; and
at least one acidic and/or basic agent to adjust the pH of the composition to 4-8, wherein the ratio of the amount of diclofenac sodium to the amount of salicylic acid ester in the gel composition is about 1:0.1 to about 1:0.5.

15. The method of claim 13, wherein topically applying a pharmaceutical gel composition of diclofenac sodium comprises applying a pharmaceutical gel composition consisting essentially of:
diclofenac sodium;
about 5-25% w/w of a glycol solvent;
about 1-6% w/w of at least one gelling agent;
about 0.01-0.75% w/w of at least one preservative;
about 0.01-1% w/w of at least one antioxidant;
about 1-10% w/w of salicylic acid ester;
about 0.05-1% w/w of menthol;
at least 50% w/w of water; and
at least one acidic and/or basic agent to adjust the pH of the composition to 4-8.

16. The method of claim 13, wherein topically applying a pharmaceutical gel composition of diclofenac sodium comprises applying a pharmaceutical gel composition consisting of:
diclofenac sodium;
about 5-25% w/w of a glycol solvent;
about 1-6% w/w of at least one gelling agent;
about 0.01-0.75% w/w of at least one preservative;
about 0.01-1% w/w of at least one antioxidant;
about 1-10% w/w of salicylic acid ester;
about 0.05-1% w/w of menthol;
at least 50% w/w of water; and
at least one acidic and/or basic agent to adjust the pH of the composition to 4-8.

17. The method of claim 13, wherein once-a-day administration of said composition provides steady state blood levels of diclofenac in the range of about 5 ng/ml to about 30 ng/ml.

18. The method of claim 13, wherein once-a-day administration of said composition provides steady state blood $C_{max}$ levels of diclofenac in the range of about 5 ng/ml to about 50 ng/ml, steady state blood $C_{min}$ levels of diclofenac in the range of about 5 ng/ml to about 20 ng/ml, and steady state AUC in the range of about 10 ng/ml*hr to about 100 ng/ml*hr.

19. The method of claim 13, wherein the composition topically applied is devoid of a $C_2$ to $C_4$ alkanol, monoalkyl ether of diethylene glycol, or fatty alcohol.

20. A method of treating or providing the relief of joint pain of osteoarthritis in one or more of the knees, ankles, feet, elbows, wrists, hands, spine, hip, and shoulder, the method comprising
topically applying once per day a pharmaceutical gel composition comprising diclofenac sodium, the diclofenac sodium being present in the topical composition in an amount of at least about 10% w/w of the composition, the composition further comprising:
a glycol solvent;
at least one gelling agent;
at least one preservative;
at least one antioxidant;
salicylic acid ester;
menthol;
water;
and at least one acidic and/or basic agent,
and the composition is devoid of a $C_2$ to $C_4$ alkanol, monoalkyl ether of diethylene glycol, or fatty alcohol,
wherein the ratio of the amount of diclofenac sodium to the amount of salicylic acid ester in the gel composition topically applied is about 1:0.1 to about 1:0.5 and the ratio of the amount of diclofenac sodium to the amount of menthol in the gel composition topically applied is about 1:0.01 to about 1:0.05.

* * * * *